(12) United States Patent
Degenhardt et al.

(10) Patent No.: US 9,995,829 B2
(45) Date of Patent: Jun. 12, 2018

(54) AUTONOMOUS DETECTOR MODULE AS A BUILDING BLOCK FOR SCALABLE PET AND SPECT SYSTEMS

(75) Inventors: Carsten Degenhardt, Aachen (DE); Thomas Frach, Aachen (DE); Gordian Prescher, Cologne (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1718 days.

(21) Appl. No.: 13/132,934

(22) PCT Filed: Nov. 16, 2009

(86) PCT No.: PCT/IB2009/055107
§ 371 (c)(1),
(2), (4) Date: Jun. 6, 2011

(87) PCT Pub. No.: WO2010/067220
PCT Pub. Date: Jun. 17, 2010

(65) Prior Publication Data
US 2011/0240864 A1    Oct. 6, 2011

Related U.S. Application Data

(60) Provisional application No. 61/121,225, filed on Dec. 10, 2008.

(51) Int. Cl.
*G01T 1/20* (2006.01)
*G01T 1/164* (2006.01)
(Continued)

(52) U.S. Cl.
CPC .............. *G01T 1/1644* (2013.01); *G01T 1/00* (2013.01); *A61B 6/037* (2013.01)

(58) Field of Classification Search
CPC .................................. G01T 1/1612; G01T 1/16
(Continued)

(56) References Cited

U.S. PATENT DOCUMENTS 4,395,635 A * 7/1983 Friauf et al. .................. 250/366
5,677,536 A * 10/1997 Vickers ..................... 250/363.09
(Continued)

FOREIGN PATENT DOCUMENTS

EP    1408347 A1    4/2004
EP    1328827 B1    8/2008
(Continued)

OTHER PUBLICATIONS

Crosetto, D. B.; A Modular VME or IBM PC Based Data Acquisition System for Multi-Modality PET/CT Scanners of Different Sizes and Detector Types; 2001; IEEE; pp. 12-78.
(Continued)

*Primary Examiner* — Abra Fein

(57) ABSTRACT

When detecting scintillation events in a nuclear imaging system, time-stamping and energy-gating processing is incorporated into autonomous detection modules (ADM) (14) to reduce downstream processing. Each ADM (14) is removably coupled to a detector fixture (13), and comprises a scintillation crystal array (66) and associated light detector (s) (64), such as a silicon photomultiplier or the like. The light detector(s) (64) is coupled to a processing module (62) in or on the ADM (14), which performs the energy gating and time-stamping.

20 Claims, 5 Drawing Sheets

(51) Int. Cl.
*G01T 1/00* (2006.01)
*A61B 6/03* (2006.01)

(58) Field of Classification Search
USPC .............................. 250/362, 363.03, 363.05
See application file for complete search history.

(56) References Cited

U.S. PATENT DOCUMENTS

| | | | |
|---|---|---|---|
| 5,751,000 A * | 5/1998 | McCroskey et al. .... | 250/363.03 |
| 5,955,733 A * | 9/1999 | Orava et al. ............. | 250/370.08 |
| 6,449,331 B1 * | 9/2002 | Nutt et al. ...................... | 378/19 |
| 6,803,579 B2 | 10/2004 | Williams et al. | |
| 7,154,989 B2 | 12/2006 | Ueno et al. | |
| 7,157,014 B1 | 1/2007 | Andreaco et al. | |
| 7,297,955 B2 | 11/2007 | Amemiya et al. | |
| 8,148,695 B2 | 4/2012 | Takahashi et al. | |
| 2002/0110216 A1 | 8/2002 | Saito et al. | |
| 2004/0065465 A1 * | 4/2004 | Chappo et al. .................. | 174/66 |
| 2004/0188623 A1 | 9/2004 | Breeding et al. | |
| 2005/0006589 A1 * | 1/2005 | Joung ..................... | G01T 1/202 |
| | | | 250/370.09 |
| 2005/0024222 A1 * | 2/2005 | Nelson et al. ............. | 340/686.1 |
| 2005/0098735 A1 | 5/2005 | Heismann | |
| 2006/0011852 A1 | 1/2006 | El-Hanany et al. | |
| 2007/0096028 A1 | 5/2007 | Tanaka | |
| 2007/0102641 A1 | 5/2007 | Schmand et al. | |
| 2007/0257196 A1 | 11/2007 | Hornig | |
| 2007/0290140 A1 * | 12/2007 | Lenox et al. ............ | 250/363.04 |
| 2008/0073542 A1 * | 3/2008 | Siegel ........................... | 250/368 |
| 2008/0075342 A1 | 3/2008 | Lazuka et al. | |
| 2008/0277587 A1 * | 11/2008 | Case ..................... | G01T 1/1642 |
| | | | 250/363.07 |
| 2009/0030305 A1 * | 1/2009 | Hoogeveen .................. | 600/422 |
| 2009/0118606 A1 * | 5/2009 | Jabri ..................... | G06F 19/321 |
| | | | 600/407 |
| 2009/0159804 A1 * | 6/2009 | Shibuya et al. ......... | 250/363.03 |
| 2009/0261256 A1 * | 10/2009 | Wieczorek ............... | 250/363.05 |

FOREIGN PATENT DOCUMENTS

| | | |
|---|---|---|
| JP | 61068580 S | 8/1986 |
| JP | 2008190901 A | 8/2008 |
| WO | 2007015198 A2 | 2/2007 |

OTHER PUBLICATIONS

Rillbert, A., et al.; A General Firewire Data Acquisition Platform Applied to SPECT; 2000; IEEE; pp. 489-493.

Stenstrom, P., et al.; A New Scalable Modular Data Acquisition System for SPECT (PET); 1998; IEEE Trans. on Nuclear Science; 45(3)1117-1121.

* cited by examiner

AUTONOMOUS DETECTOR MODULE AS A BUILDING BLOCK FOR SCALABLE PET AND SPECT SYSTEMS

CROSS REFERENCE TO RELATED APPLICATIONS

This application claims the benefit of U.S. provisional application Ser. No. 61/121,225 filed Dec. 10, 2008, which is incorporated herein by reference.

The present innovation finds particular application in nuclear imaging systems, particularly involving positron emission tomography (PET) imaging and/or single photon emission computed tomography (SPECT) imaging, but may also find application in other nuclear imaging systems and the like. However, it will be appreciated that the described technique may also find application in other imaging systems, other imaging scenarios, other image analysis techniques, and the like.

Radiation detectors for PET and SPECT systems are either based on scintillator/photodetector combinations or use direct conversion materials. In both cases, substantial processing of the recorded energy depositions has to be performed in order to derive the energy and timestamp of scintillation event. For instance, many gamma rays undergo Compton scatter and distribute their energy over multiple detection elements. The individual energy depositions are collected by readout electronics to form the resulting event, and, in PET, a timestamp is attached to this so-called "single" event (e.g., energy clustering and timestamping). After energy clustering and energy gating, the event can be assigned to a detection element as the most probable first element of interaction. In case of a SPECT detector, this event can directly be used for reconstruction, whereas for PET a coincidence between two events is found prior to using the event pair for reconstruction.

In classical PET and SPECT scanners, data processing is done in a centralized manner. The output of the scintillator/photodetector combination is processed by electronics crates (e.g., cabinets housing processing electronics) performing the energy discrimination, event clustering, energy gating, pixel identification, and timestamping. Detectors using solid state light detectors or direct converters employ more readout electronics concentrated close to the detector by using dedicated front-end electronics (e.g., ASICs, such as pre-amplifiers and analog-to-digital converters).

However, classical solutions do not integrate enough electronics into one detector module to be able to operate it as an autonomous, scalable building block of a complete system. In general, this leads to readout electronics that are tailored to the exact geometry of the PET or SPECT system under consideration. Therefore, even slight changes to the geometry can be difficult to implement without changing large parts of the readout electronics. In addition, the late clustering of individual events leads to high data rates that have to be processed by the readout electronics, since energy gating can only be applied far down the processing chain.

The present application provides new and improved systems and methods for including processing electronics in a nuclear detector module to provide a scalable nuclear detector architecture, which overcome the above-referenced problems and others.

In accordance with one aspect, a nuclear scanning detector system includes a nuclear scanner comprising a plurality of nuclear detectors, and a plurality of autonomous detector modules (ADM) removably coupled to each detector. Each ADM includes a scintillation crystal array comprising one or more scintillation crystals, one or more light detectors for detecting scintillation events in the scintillation crystal array, and a processing module that timestamps each detected scintillation event, executes an energy-gating protocol to discriminate gamma rays that underwent Compton scatter, and outputs time-stamped, energy-gated scintillation event information.

In accordance with another aspect, a method of reducing downstream data processing demand in a nuclear imaging system includes detecting scintillation events in one or more autonomous detector modules (ADM), time-stamping the scintillation events at the module-level on each ADM, and performing an energy-gating technique on the scintillation events at the module-level; outputting time-stamped, energy-gated scintillation event information. The method further includes processing and reconstructing the event information into a 3-D image volume.

According to another aspect, an autonomous detector module (ADM) includes a scintillation crystal array, at least one light detector that detects a scintillation event in all or a portion of the scintillation crystal array, and a processing module that time-stamps detected scintillation events, executes an energy-gating technique on the detected scintillation events and outputs time-stamped, energy-gated scintillation event information. The at least one light detector is coupled to all or a portion of the scintillation crystal array at a first side, and to a connector at a second side. The connector removably couples the at least one light detector to a printed circuit board (PCB) that is coupled to the processing module.

One advantage is that downstream data processing overhead is reduced.

Another advantage resides in scalability of detector architecture using replaceable and interchangeable detector modules.

Still further advantages of the subject innovation will be appreciated by those of ordinary skill in the art upon reading and understand the following detailed description.

The innovation may take form in various components and arrangements of components, and in various steps and arrangements of steps. The drawings are only for purposes of illustrating various aspects and are not to be construed as limiting the invention.

Figure 1:
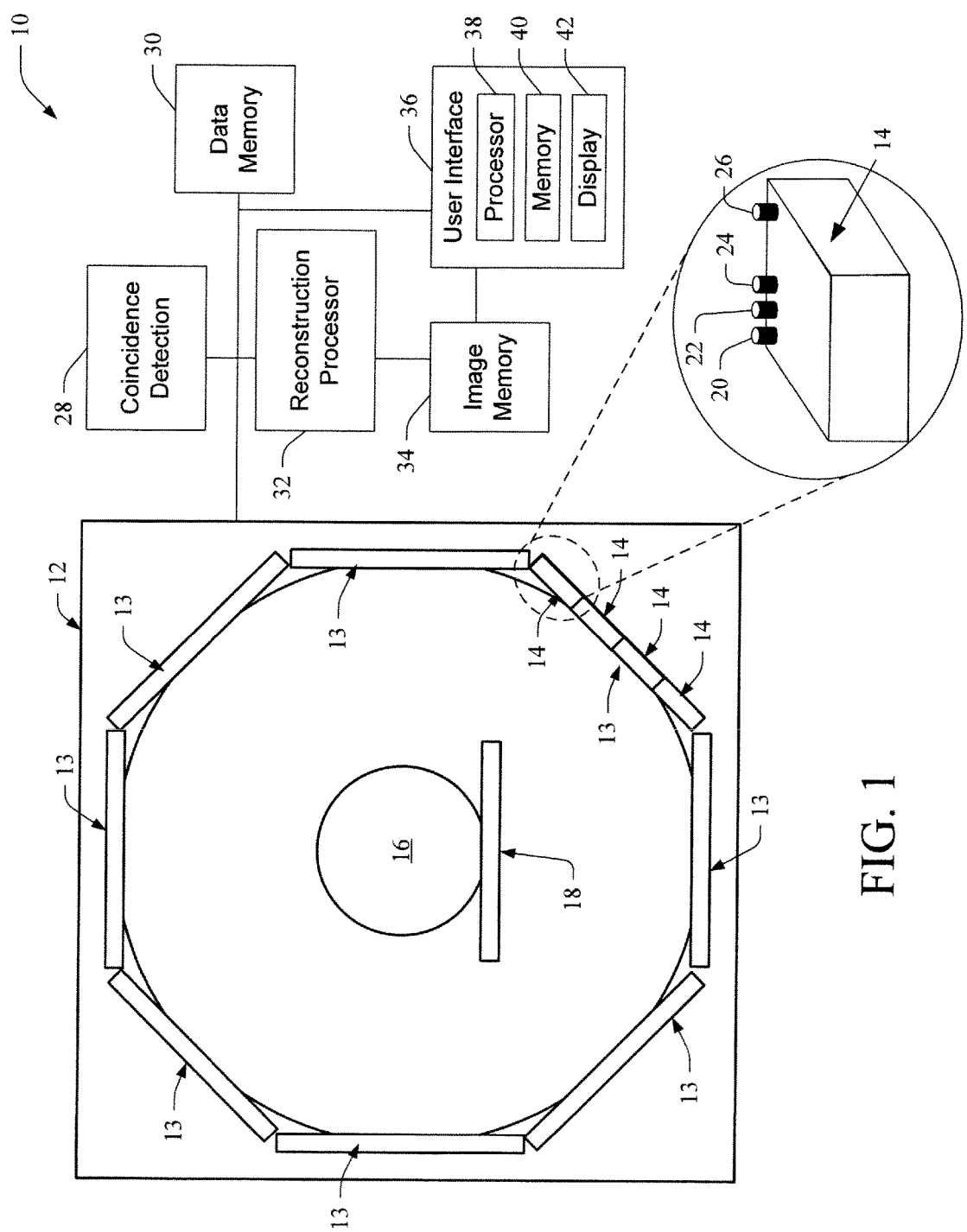
FIG. 1 illustrates a nuclear imaging system comprising a nuclear scanner (e.g., a PET or SPECT scanner) with a plurality of detectors, each of which includes an array of autonomous detector modules (ADM) that incorporate all of the processing electronics needed to generate or detect energy-gated single scintillation events.

FIG. 1 illustrates a nuclear imaging system 10 comprising a nuclear scanner 12 (e.g., a PET or SPECT scanner) with a plurality of mechanical detector fixtures (e.g., detector heads) 13, each of which includes an array of autonomous detector modules (ADM) 14 that incorporate all of the processing electronics needed to generate or detect energy-gated single scintillation events. The ADM facilitates providing a fully scalable nuclear scanner architecture that simplifies system design and facilitates easy implementation of different nuclear scanner geometries. In addition, the ADM facilitates lower data rates in downstream processing electronics, making it especially applicable to high count-rate applications.

A plurality of detector fixtures 13 are positioned around an examination region of the scanner 12 to image a subject or patient 16 positioned on a subject support 18. Each ADM 14 includes a plurality of input/output (I/O) pins or connectors, including a power connection 20 for providing power to the ADM, a clock connection 22 that facilitates time-stamp generation, a configuration connection 24 via which the ADM is configured, and an output connection 26 via which scintillation event data is output. In one embodiment, the I/O connectors are bundled into a single connector or bus. Thus, the ADM includes a complete set of processing electronics for generating or detecting single scintillation events, within the detector housing. This facilitates providing an autonomous module that is fed by a power supply, includes a system clock and a configuration port, and that outputs energy-gated single scintillation events. In this manner, the ADM provides a scalable building block for PET and SPECT detectors 13.

In SPECT imaging, a projection image representation is defined by the radiation data received at each coordinate on the detector. In SPECT imaging, a collimator defines the rays along which radiation is received. In PET imaging, the detector outputs are monitored for coincident radiation events on two detectors. From the position and orientation of the detectors and the location on the detector faces at which the coincident radiation is received, a ray or line of response (LOR) between the coincident event detection points is calculated. This ray defines a line along which the radiation event occurred. In both PET and SPECT, the radiation data from a multiplicity of angular orientations of the detectors is stored to a data memory 30, and reconstructed by a reconstruction processor 32 into a volumetric image representation of the region of interest, which is stored in the volume image memory.

In PET, scintillation events (e.g., gamma ray interactions with one or more scintillation crystals) detected by the ADM 14 are time-stamped and energy-gated (e.g., to discriminate against gamma rays that underwent Compton scatter in the examined subject, etc.), and output to a coincidence detection component 28 that analyzes time stamped scintillation event information to identify scintillation event pairs that correspond to a common annihilation event in the subject 16 during the nuclear scan. The data memory 30 stores raw scintillation event information, timestamp information, and/or other acquired nuclear scan data, as well as coincidence detection information and the like. The reconstruction processor 32 reconstructs the nuclear scan data into one or more nuclear images, which are stored to an image memory 34 and rendered on a user interface 36. The user interface includes one or more processors 38 (e.g., data processors, video processors, graphical processors, etc.) and a memory 40 that facilitate outputting nuclear image data on a display 42 to a user, as well as receiving and/or processing user input.

Each ADM 14 includes an array of scintillators and photodetectors (not shown in FIG. 1), along with the appropriate circuitry to perform part of the information processing. Specifically, energy window gating and the time-stamping functions for detected scintillation events are performed in each ADM. This has the advantage of weeding-out events where the gamma ray underwent one or more Compton scatters within the examined object. Since this weeding-out is done at the module level, it greatly reduces the number of time-stamped events that are sent along bus lines for further processing. This feature significantly reduces the processing load on downstream components. Specifically, downstream components may be streamlined to include coincidence detection and reconstruction, without requiring downstream time-stamp and/or gating processing.

In one embodiment, the ADM processing circuitry includes correction circuitry for Compton scatter within the scintillator array. Since scintillator materials have a finite stopping power for gamma radiation, a gamma ray sometimes deposits its energy in multiple scintillator crystals. If the module is too small, a significant portion of the Compton-scattered radiation may be deposited partially in two or more different modules and may be lost due to the fact that the energy gating is done on the module level. Accordingly, the size of the module constitutes a compromise between the size of the module and the fraction of events one can afford to loose. The size is dependent on the density or radiation stopping power of the scintillators employed therein. Approximately 97% of the Compton-scattered radiation can be recovered in a 7×7 $cm^2$ module with Lutetium Yttrium Orthosilicate (LYSO) or Lutetium Orthosilicate (LSO), or variants thereof (e.g., Cerium doped variants, etc.). A less dense scintillator such as Lanthium Bromide (LaBr) can be employed in a larger module, such as a 10×10 $cm^2$ module. A higher density scintillator such as a Bismuth Germanate (BGO) scintillator can employ a smaller element array, such as a 4×4 $cm^2$ module. In general, the smaller the module, the less processing power is needed for each module, but the more data that may be lost.

In one embodiment, the ADM 14 is partitionable into smaller effective modules, such as 2×2 or 4×4 modules. The scintillator/detector combination can comprise Anger-logic configurations including a lightguide or a one-to-one coupling between scintillators and detectors. In another embodiment, each ADM includes arrangements of scintillators and diodes and an on-board processing circuit to measure depth of interaction. In yet another embodiment, the on-module circuitry includes a flash memory which may store data correction tables, buffer data, or the like. In yet another embodiment, the detector elements and the processing electronics share two sides of the same PCB.

The use of standardized ADMs enables a detector module to be replaced with a pre-calibrated ADM that mitigates a need for recalibrating the scanner. For instance, if it is determined that an ADM is faulty (e.g., based on poor or absent signals from the ADM or the like), then a fault signal is sent to alert a technician or the like of the faulty ADM, which is then replaced by the technician with a new, pre-calibrated ADM. Moreover, the use of standardized ADMs facilitates scanner design. This also facilitates the development of modules with different sizes of scintillators and detectors for achieving different sensitivities and spatial resolutions. The standardized module approach enables modules of different sizes to be used in the same scanner. Analogously, modules within a scanner can be swapped out, without recalibration, to change its resolution.

Figure 2:
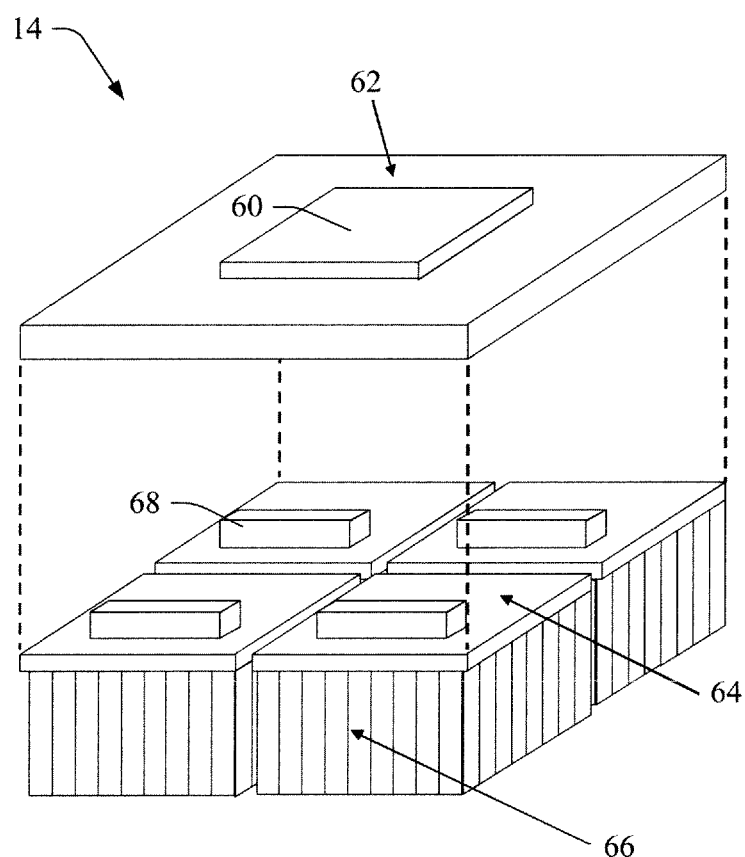
FIG. 2 is an illustration of the ADM and various components thereof, in accordance with one or more aspects described herein.

FIG. 2 is an illustration of the ADM 14 and various components thereof, in accordance with one or more aspects described herein. The ADM includes a processing module 60 (e.g., one or more processors and associated memory) on a printed circuit board (PCB) 62. The processing module 60 has stored thereon one or more field-programmable gate arrays (FPGA) or the like for time-stamping and gating detected scintillation events. Additionally or alternatively, the processing module has one or more application-specific integrated circuits (ASIC) for time-stamping and gating detected scintillation events. Additionally or alternatively, the time stamping circuit is integrated into the light detectors, outputting digital values for timestamp and energy of a gamma hit to the processing electronics.

A plurality of solid state light detectors 64, such as arrays or tiles of silicon photomultipliers (SiPMs), avalanche photodiodes (APDs), or the like, are coupled to respective portions of a scintillation crystal array 66. In FIG. 2, each light detector is coupled to an 8×8 sector of crystals, and the four illustrated tiles combine to form a 16×16 crystal array 66. Each light detector 64 is also coupled to a connector 68 that connects the light detector 64 to the PCB 62, and thus to the processing module 60 containing one more multiple ASICs and/or FPGAs. Alternatively, the detector elements and the processing electronics share two sides of the same PCB. The scintillator facing face of each tile is filled as close to the edges as possible with the SiPMs or APDs. In this manner, the tiles can be closely packed while maintaining a consistent pixel size and periodicity across the tiles. Although shown in a rectangular grid, the tiles can be offset, e.g., offset rows or columns.

Since energy-clustering (e.g., detection and aggregation of multiple scintillation events from a single gamma photon) is performed at the module level, the energy gating is performed at the module level as well. Depending on the patient or subject size, this facilitates a reduction of the data rate to be processed by the downstream electronics by a factor of 5 to 10. The data output of the module delivers the complete information to characterize an event, including interaction crystal identity (e.g., the identities or coordinates of one or more crystals in which a scintillation event is detected), energy, and timestamp information. Therefore, the output of all individual ADMs can be inserted into a single coincidence detection circuitry (e.g., for PET), or directly used for reconstruction (e.g., for SPECT).

In one embodiment, individual light detectors 64 (and their associated sectors of the module's crystal array 66) can be replaced individually within the ADM 14. For instance, the connector 68 can provide both an electrical connection to the processing module 60 through the PCB 62 and a mechanical connection to the PCB to make the light detector 64 removable for replacement should the detector 64 fail. Additionally, or alternatively, each ADM 14 is removably coupled to its detector 13 (FIG. 1), such that a particular ADM can be removed and replaced to ensure that all ADMs in an array of ADMs on a detector are functional.

In another embodiment, ADMs of different sizes are employed on a given detector to facilitate creating detector surfaces of varied geometries and/or sensitivity.

In another embodiment, readouts from the individual modules are provided to coincidence detection electronics (not shown). The processing modules of neighboring ADMs can employ a nearest-neighbor type communication protocol to decide which processing module processes Compton-type data when the modules are small enough (e.g., 8×8 crystal arrays or some other relatively small array size) that Compton events may be detected at two or more neighboring modules.

In yet another embodiment, each processing module 60 includes flash memory (not shown) with one or more correction tables stored thereon for processing scintillation event data. The correction tables facilitate accounting for Compton scatter and the like.

Figure 3:
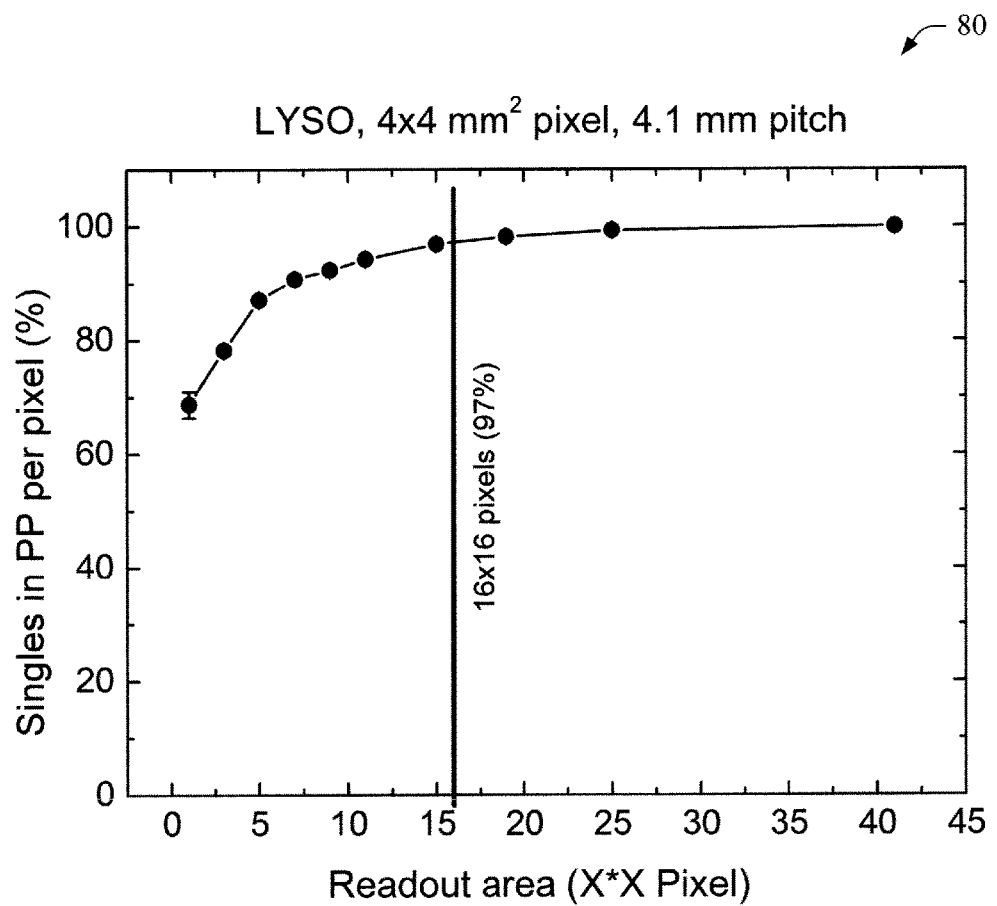
FIG. 3 illustrates a graph that shows the dependence of detected single events on module size.

FIG. 3 illustrates a graph 80 that shows the dependence of detected single events on module array size. The graph shows a percentage of detected scintillation events per pixel plotted as a function of pixel readout area for a 4×4 mm$^2$ pixel LYSO scintillator crystal array with 4.1 mm pitch. For smaller modules, Compton scatter into neighboring modules leads to a loss in single event detection sensitivity. For a module array size of 16×16 crystals, as few as 3% of all single events are lost due to Compton scatter into neighboring modules, constituting a suitable module size of approx. 7×7 cm$^2$.

Since energy-gating is performed in the ADM, it is desirable to ensure that Compton scatter into neighboring modules does not lead to a loss of system sensitivity. The system simulation graph 80 shows that for module sizes of 16×16 crystals (e.g., 4×4 mm$^2$ each), only approximately 3% of all single events are lost due to Compton scatter into neighboring modules. This illustrates that a module size of 7×7 cm$^2$ constitutes a suitable module size.

In general, module size is a function of scintillation material density. For instance, when using a LYSO or LSO scintillation material, a 16×16 crystal array may be employed. When using an LaBr scintillation material, a 24×24 crystal array may be employed. In another example, an 8×8 crystal array is employed when a BGO scintillation material is used. It will be appreciated that the foregoing examples of crystal array size are illustrative in nature, and intended to illustrate that as scintillation density increases, the chosen module size can be decreased.

Figure 4:
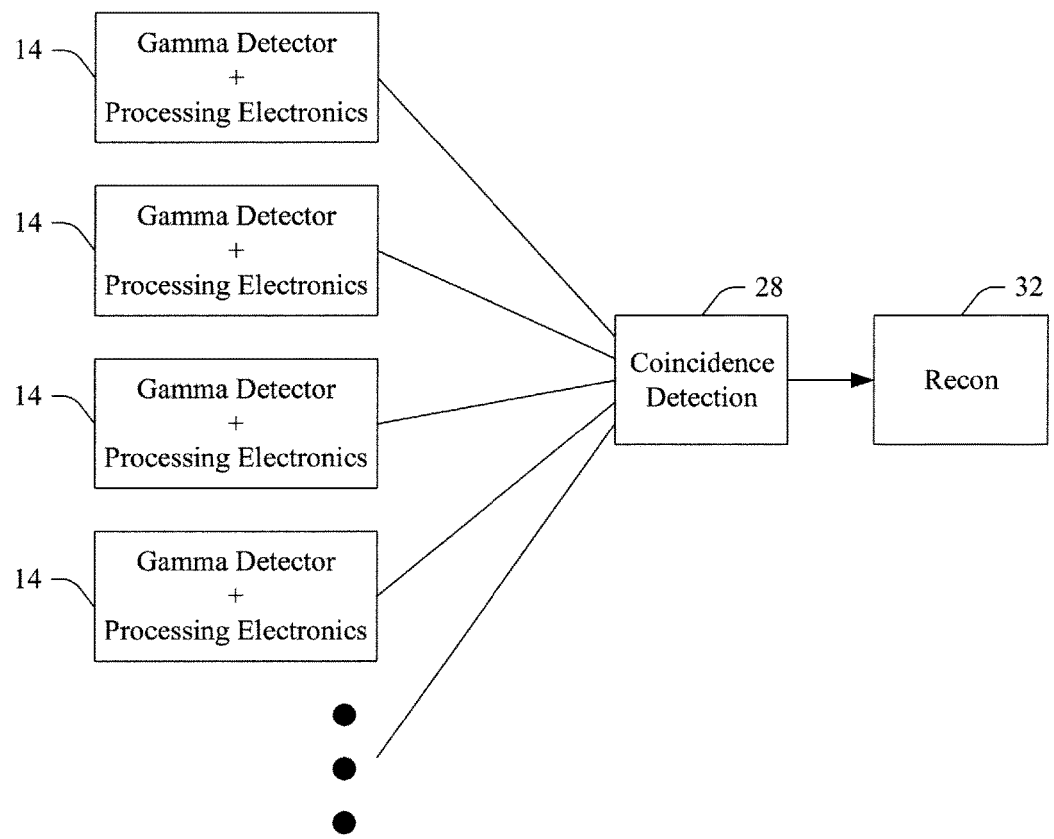
FIG. 4 illustrates a possible PET system architecture that is facilitated by the use of ADMs, in accordance with one or more aspects described herein.

FIG. 4 illustrates a possible PET system architecture 100 that is facilitated by the use of ADMs 14, in accordance with one or more aspects described herein. The coincidence detection circuitry 28 receives energy-gated single event data from a plurality of detector modules 14. Since energy gating is done at the module level, the data rate input into the coincidence detection circuitry is reduced by a factor of 5 to 10 (depending on patient size) compared to classical architectures. Once coincidence detection has been performed, paired energy-gated scintillation event data is provided to the reconstruction processor 32, which reconstructs an anatomical image for display to a user.

Figure 5:
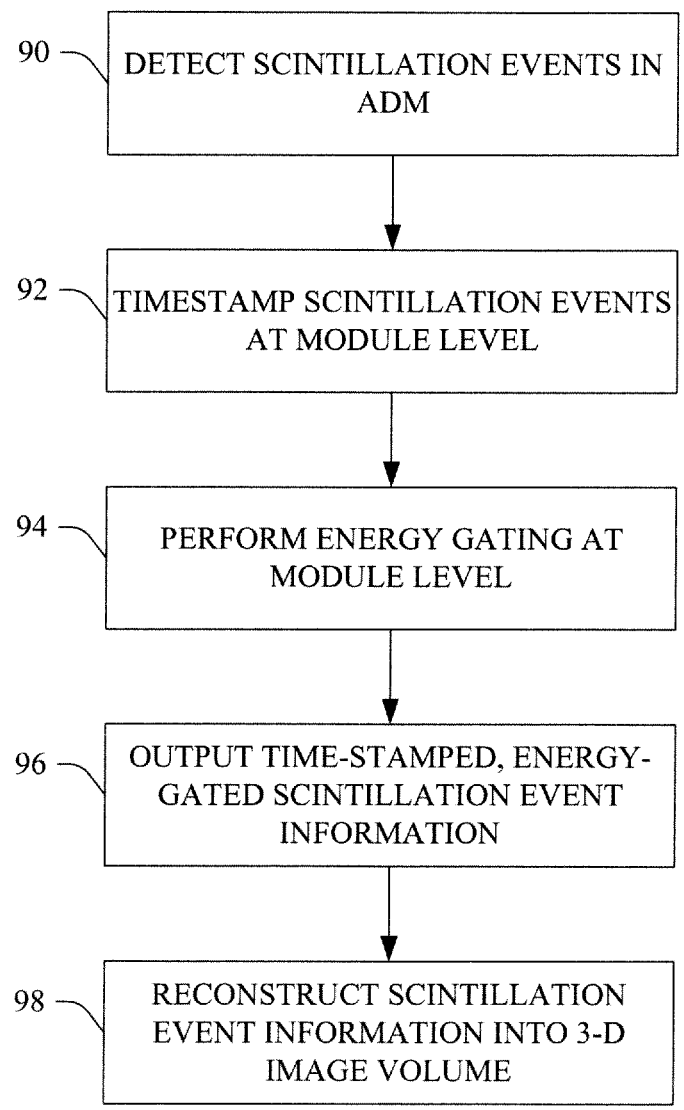
FIG. 5 illustrates a method of performing scintillation event time-stamping and energy gating at the detector module level, rather than processing detected scintillation events downstream, in order to reduce downstream data processing requirements, in accordance with one or more aspects described herein.

FIG. 5 illustrates a method of performing scintillation event time-stamping and energy gating at the detector module level, rather than processing detected scintillation events downstream, in order to reduce downstream data processing requirements, in accordance with one or more aspects described herein. At 90, scintillation events are detected in an ADM 14. At 92, scintillation event information is time-stamped at the module level, for example, by time-stamping circuitry included in a processor module in the ADM. At 94, the scintillation events are energy-gated at the module level (e.g., by the ADM in which the scintillation events are detected). At 96, time-stamped, energy-gated scintillation event information is output for processing and/or reconstruction. By time-stamping and energy-gating the scintillation event information at the ADM, these processing actions are removed from the downstream processing workflow, thereby increasing reconstruction speed. At 98, the time-stamped and energy-gated scintillation event information is reconstructed into a 3-D image volume.

In one embodiment, the method further includes executing a coincidence detection algorithm on the output scintillation event information to identify corresponding pairs of scintillation events prior to reconstructing the 3-D image volume.

In another embodiment, the method includes determining that an ADM is faulty (e.g., by detecting a lack of signal therefrom, or in any other suitable manner), and transmitting a fault signal that alerts a technician of the one or more faulty ADMs. The technician can then replace the faulty ADM with a new pre-calibrated ADM.

The described systems and methods can be applied to PET and SPECT detectors. The fully scalable architecture enables a simplified system design and facilitates geometrical design freedom of the scanner. This in turn leads to drastically reduced data rates that have to be handled by downstream electronics. Especially for high count-rate applications, the described systems and methods mitigate a need for high-bandwidth processing electronics.

Additionally, the described methods may be stored on a computer-readable medium as computer-executable instructions that are executed by a processor or processors.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

The invention claimed is:

1. A nuclear scanning detector system, including:
   a nuclear scanner comprising a plurality of nuclear detector fixtures;
   one or more autonomous detector modules (ADM) removably coupled to each detector fixture, each ADM including:
      a scintillation crystal array comprising one or more scintillation crystals;
      one or more removable light detectors for detecting scintillation events in respective sectors of the scintillation crystal array;
      a processing module that timestamps each detected scintillation event, executes an energy-gating protocol to identify Compton scattered events, and outputs time-stamped, energy-gated scintillation event information; and
      a configuration connector via which the ADM is configured during setup.

2. The system according to claim 1, further including:
   a coincidence detection component that receives the time-stamped, energy-gated scintillation event information from the plurality of ADMs and identifies pairs of detected scintillation events that correspond to a single annihilation event in a subject.

3. The system according to claim 2, further including:
   a reconstruction processor that reconstructs an image volume of a subject from the identified pairs of scintillation events;
   an image memory that stores the reconstructed image volume; and
   a display on which the image volume is displayed to a viewer.

4. The system according to claim 1, wherein each ADM includes:
   a power connector via which the ADM receives power;
   a clock connector via which the ADM receives timing information from a master clock for time-stamping detected scintillation events; and
   an output connection via which the ADM transmits the time-stamped, energy-gated scintillation event information;
   wherein the connections and corresponding connectors on a gantry have a plug-socket relationship.

5. The system according to claim 1, wherein the scintillation crystal array has dimensions in the range approximately 3×3 cm2 to approximately 16×16 cm2.

6. The system according to claim 5, wherein the scintillation crystals are formed of one of:
   Bismuth Germanate (BGO) with the scintillation crystal array having dimensions in the range of approximately 3×3 cm2 to approximately 6×6 cm2; or
   at least one of Lutetium Yttrium Orthosilicate (LYSO) or Lutetium Orthosilicate (LSO) with the scintillation crystal array having dimensions in the range of approximately 3×3 cm2 to approximately 8×8 cm2; or
   Lanthium Bromide (LaBr) with the scintillation crystal array having dimensions in the range of approximately 6×6 cm2 to approximately 12×12 cm2.

7. The system according to claim 1, wherein the light detectors each include a plurality of light sensitive elements arranged on a tile, each tile having light sensitive elements corresponding to a plurality of detector pixels with the light sensitive elements substantially covering the tile with minimal edge regions such that the tiles can be mounted abutting each other and maintain consistent detector pixel periodicity.

8. The system according to claim 7, wherein the tiles are rectangular and each module includes at least four tiles in a close-packed relationship.

9. The system according to claim 1, wherein the processing module includes flash memory that stores a lookup table including correction information used by the processing module to compensate for Compton-type scatter.

10. The system according to claim 1, wherein the processing module includes at least one of field-programmable gate arrays (FPGAs) and application-specific integrated circuits (ASICs) for time-stamping and energy-gating detected scintillation events.

11. The system according to claim 1, wherein the processing module includes at least one field-programmable gate array (FPGA) that receives timestamp information from a time-stamping unit integrated into the light detector.

12. A method of reducing downstream data processing demand in a nuclear imaging system, including:
   detecting scintillation events in one or more autonomous detector modules (ADM) each comprising a plurality of removable light detectors;
   time-stamping the scintillation events at the module-level on each ADM;
   aggregating multiple scintillation events from a single gamma photon;
   performing an energy-gating technique on the scintillation events at the module-level;
   outputting time-stamped, energy-gated scintillation event information; and
   processing and reconstructing the event information into a 3-D image volume; and
   determining that one or more ADMs is faulty;
   transmitting a fault signal that alerts a technician of the one or more faulty ADMs; and
   replacing the one or more faulty ADM with a new pre-calibrated ADM.

13. The method according to claim 12, further including:
   executing a coincidence detection algorithm on the output scintillation event information to identify corresponding pairs of scintillation events.

14. A non-transitory computer-readable medium having stored thereon computer-executable instructions for performing the method according to claim 12.

15. An autonomous detector module (ADM), including:
a scintillation crystal array;
at least one light detector that detects a scintillation event in all or a portion of the scintillation crystal array;
a processing module that time-stamps detected scintillation events or receives timestamp and energy information from a circuit integrated with the light detector, executes an energy-gating technique on the detected scintillation events and outputs time-stamped, energy-gated scintillation event information; and
a connector that removably couples the at least one light detector to a printed circuit board (PCB) that is coupled to the processing module; and
a configuration connector via which the ADM is configured during at least one of setup or during a scan.

16. The ADM according to claim 15:
wherein the at least one light detector is coupled to all or a portion of the scintillation crystal array at a first side, and to the connector at a second side.

17. The ADM according claim 15:
wherein the at least one light detector is coupled to all or a portion of the scintillation crystal array at a first side, and to a printed circuit board (PCB) at a second side, the printed circuit board being further coupled to the processing module.

18. The ADM according to claim 15, further including:
a power connector via which the ADM receives power;
a clock connector via which the ADM receives timing information from a master clock for time-stamping detected scintillation events; and
an output connection via which the ADM transmits the time-stamped, energy-gated scintillation event information.

19. A positron emission tomography (PET) imaging system including a plurality of the ADMs according to claim 15.

20. An autonomous detector module (ADM) comprising:
a plurality of tiles arranged in a close-packed array, each tile including:
a plurality of light sensitive elements corresponding to a plurality of detector pixels with the light sensitive elements substantially covering the tile with minimal edge regions, and
at least one scintillator optically coupled to the light sensitive elements;
wherein the tiles are removably mounted abutting each other with the light sensitive elements of one tile being sufficiently adjacent to the light sensitive elements of an adjacent tile that a consistent detector pixel periodicity is maintained across the plurality of tiles; and
a configuration connector via which the ADM is configured during setup.

* * * * *